(12) United States Patent
Tortelli et al.

(10) Patent No.: US 8,536,387 B2
(45) Date of Patent: Sep. 17, 2013

(54) PROCESS FOR THE SYNTHESIS OF PERFLUOROBUTADIENE

(75) Inventors: Vito Tortelli, Milan (IT); Stefano Millefanti, Carbonate (IT); Serena Carella, Parabiago (IT)

(73) Assignee: Solvay Solexis. S.p.A., Bollate (IT)

( * ) Notice: Subject to any disclaimer, the term of this patent is extended or adjusted under 35 U.S.C. 154(b) by 428 days.

(21) Appl. No.: 12/808,410

(22) PCT Filed: Dec. 24, 2008

(86) PCT No.: PCT/EP2008/068288
§ 371 (c)(1),
(2), (4) Date: Jun. 16, 2010

(87) PCT Pub. No.: WO2009/087067
PCT Pub. Date: Jul. 16, 2009

(65) Prior Publication Data
US 2010/0280291 A1  Nov. 4, 2010

(30) Foreign Application Priority Data
Jan. 8, 2008 (EP) .................................. 08425007

(51) Int. Cl.
*C07C 17/23* (2006.01)
(52) U.S. Cl.
USPC ............................ 570/155; 570/156; 570/158
(58) Field of Classification Search
USPC ......................................... 570/155, 158, 156
See application file for complete search history.

(56) References Cited

U.S. PATENT DOCUMENTS

| | | | |
|---|---|---|---|
| 2,668,182 A | | 2/1954 | Miller |
| 2,894,042 A * | | 7/1959 | Miller ........................... 570/158 |
| 3,046,304 A | | 7/1962 | Neville |
| 3,639,102 A * | | 2/1972 | Grakauskas .................. 423/466 |
| 3,673,252 A * | | 6/1972 | Coon ............................ 564/116 |
| 3,897,502 A * | | 7/1975 | Russell et al. ................ 568/683 |
| 3,953,585 A * | | 4/1976 | Sukornick .................... 423/489 |
| 6,362,109 B1 | | 3/2002 | Kim et al. |
| 6,387,287 B1 | | 5/2002 | Hung et al. |
| 2007/0203368 A1* | | 8/2007 | Tortelli et al. ................ 568/685 |
| 2009/0216054 A1 | | 8/2009 | Ohno et al. |

FOREIGN PATENT DOCUMENTS

| | | |
|---|---|---|
| EP | 1247791 A1 | 10/2002 |
| EP | 1801090 A2 | 6/2007 |
| RU | 2246478 C1 | 2/2005 |
| RU | 2264376 C1 | 11/2005 |
| RU | 2272017 C2 | 3/2006 |
| WO | WO 2007125975 A1 | 10/2010 |

OTHER PUBLICATIONS

Barbour A.K. et al, "The Preparation of Organic Fluorine Compounds by Halogen Exchange", Adv. Fluorine Chem., 1963, 3, p. 194-201 (9 pg.).
Vecchio M. et al, "Studies on a vapour-phase process for the manufacture of chlorofluoroethanes", Journal of Fluorine Chemistry, 1974, 4, p. 117-139, Elsevier Sequoia S.A., Lausanne, Switzerland (23 pg.).
Kvicala J. and Paleta O., 4.2. "Dehalogenation in Methods of Organic Chemistry (Houben-Weyl)", 1999, vol. E 10 B2, p. 125-161, G. Thieme (37 pg.).

* cited by examiner

Primary Examiner — Joseph Kosack
Assistant Examiner — Matthew Coughlin
(74) Attorney, Agent, or Firm — Arent Fox LLP

(57) ABSTRACT

Process for preparing perfluoro-1,3-butadiene, comprising the following steps:
A) preparation of fluoro-halo-butanes of formula:

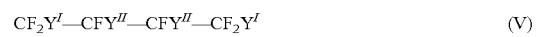

$$CF_2Y^I\text{—}CFY^{II}\text{—}CFY^{II}\text{—}CF_2Y^I \quad (V)$$

in which $Y^I$ and $Y^{II}$, which may be identical or different, may be H, Cl or Br, with the condition that $Y^I$ and $Y^{II}$ are not simultaneously hydrogen;
starting with a chloroolefin having the formula:

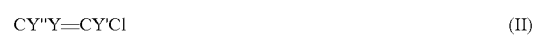

$$CY"Y\text{=}CY'Cl \quad (II)$$

in which Y, Y', Y", which may be identical or different, are H, Cl or Br, with the condition that Y, Y', Y" are not simultaneously hydrogen;
and performing the following steps:
a fluorodimerization, and
a fluorination with elemental fluorine,
the order of the two steps also possibly being inverted,
a dehalogenation or dehydrohalogenation step being performed between the two steps,
B) dehalogenation or dehydrohalogenation of the fluoro-halo compounds of formula (V) to give the compound perfluoro-1,3-butadiene.

17 Claims, No Drawings

PROCESS FOR THE SYNTHESIS OF PERFLUOROBUTADIENE

CROSS-REFERENCE TO RELATED APPLICATIONS

This application is a U.S. national stage application under 35 U.S.C. §371 of International Application No. PCT/EP2008/068288 filed Dec. 24, 2008, which claims priority to European Patent Application No. 08425007.5 filed Jan. 8, 2008, this application being incorporated herein by reference in its entirety for all purposes.

The present invention relates to a process for synthesizing fluorohalobutanes, which, via dehalogenation or dehydrohalogenation, give perfluoro-1,3-butadiene. More particularly, the present invention relates to a process for obtaining perfluoro-1,3-butadiene with good selectivity in the individual steps, which may be obtained without expensive processes for separating out hydrogenated by-products, using precursors that do not belong to the category of chlorofluorocarbons (CFCs).

It is well known that, as a result of their impact on the ozone layer (ODP) and of their high environmental impact (GWP), CFCs have been banned or limited by the Montreal protocol and subsequent amendments thereof. In any case, in the few sectors in which they are still used, there is a need to avoid CFCs becoming dispersed into the environment. In addition, in industrial CFC production processes, the desired compound that is formed is always a mixture with other products of similar structure. The said other products must be separated out, at added cost.

It is also known that perfluoro-1,3-butadiene is a stable gas (boiling point 5.5° C.) and that it is used in applications in the semiconductor industry. See, for example, U.S. Pat. Nos. 6,362,109 and 6,387,287. This compound is highly efficient and selective in the plasma etching of silicon wafers and simultaneously ensures low emissions of perfluorocarbons. It has been confirmed that this product has a negligible effect on the GWP (Global Warming Potential). In addition, perfluorobutadiene does not damage the ozone layer (ODP) since it does not contain chlorine.

Processes for preparing perfluoro-1,3-butadiene, comprising the synthesis of precursors of halofluorocarbons (halofluorocarbons CFC) are known. U.S. Pat. No. 2,668,182 relates to the synthesis of polyunsaturated fluoro(halo)olefins containing at least three and more particularly from 4 to 12 base carbon atoms in the molecule, and containing at least two double bonds. The preferred compounds are halo fluorobutadienes of formula:

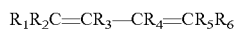

in which at least one substituent R is fluorine and the remaining are halogen or other groups such as nitro and cyano. The process for preparing them comprises two different synthetic schemes.

The first comprises the thermal dimerization of a halofluorinated olefin followed by treatment with zinc. The first step of this process is as follows:

in which X is a halogen other than fluorine, preferably chlorine, and at least one of the substituents R is fluorine, the others being halogen, perfluoroalkyl or perfluoroaryl. In the second step, the compound obtained is treated with zinc to remove the substituent X and to introduce a double bond between positions 3 and 4.

The second process comprises the dimerization of a chlorofluoroolefin with elemental fluorine, followed by dechlorination with zinc. In the first step of this process, the following reaction takes place:

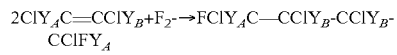

in which Y may be F, Cl, perfluoroalkyl or perfluoroaryl. In the second step, the compound obtained is dehalogenated by treatment with zinc. The said patent, in particular Example 3 thereof, describes the dimerization of 1,2-dichloro-1,2-difluoroethylene (CFC 1112) with fluorine to give 1,2,3,4-tetrachlorohexafluorobutane (CFC 316), which is reacted with zinc to give perfluoro-1,3-butadiene. The CFC 1112 used as precursor is usually prepared by dehalogenation of tetrachlorodifluoroethane $CCl_2FCCl_2F$ (CFC 112) with zinc metal in an alcoholic solvent. See, for example, Houben Weyl vol. E 10 B2, pp. 125-161. Industrially, CFC 112 is obtained as a component of a mixture of various symmetrical and unsymmetrical chlorofluoroethanes, mainly the following: CFC 113 ($CF_2Cl$—$CFCl_2$) and CFC 114 ($CF_2Cl$—$CF_2Cl$). The latter chlorofluoroethanes were the ones of major industrial interest since they were used as coolants and solvents. The methods for synthesizing these mixtures of chlorofluoroethanes are given, for example, in Adv. Fluorine Chem. 3 (1963), "The Preparation of Organic Fluorine Compounds by Halogen Exchange" pp. 194-201, Fluorine Chem. 4 (1974) 117-139. It is no longer possible to use the compounds CFC 113 and 114, pursuant to the Montreal Protocol and its subsequent amendments as reported hereinabove. In addition, CFC 112, and consequently CFC 1112, are no longer industrially available. Furthermore, it is noted that, in the described processes, CFC 112 is obtained as a mixture with its isomer CFC 112a. This isomer is formed in large amounts, occasionally in greater percentage relative to CFC 112. See J. Fluorine Chem. 4 (1974) 117-139. CFC 112 and CFC 112a have very similar boiling points, of 92.8° C. and 91.5° C., respectively. They are therefore difficult to separate via fractional distillation. Thus, if it is desired to obtain CFC 112 as pure as possible, low distillation yields are obtained, since the product is lost by entrainment together with the CFC 112a. It should also be pointed out that, in the subsequent dechlorination to obtain CFC 1112, the CFC 112a when present leads to the formation of CFC 1112a, which, as is well known, is a highly toxic product. From an industrial viewpoint, CFC 112a should therefore be reduced to very low levels. However, as stated, this leads to very high losses of the product of interest, CFC 112.

U.S. Pat. No. 3,046,304 describes a method for dimerizing compounds of formula RC(X)(Y)(Z), in which Z is Cl, Br or iodine; Y is a halogen atom having an atomic weight less than Z, X is H, halogen with an atomic weight less than Z, R is alkyl, haloalkyl or alkenyl. Heat or radiation, for instance ultraviolet light, infrared rays, etc., is used in the process, to produce a product of general formula RC(X)(Y)—C(X)(Y)R. Halogen-atom acceptors such as zinc, magnesium, mercury, etc. may also be used. The products obtained may be dehalogenated or dehydrohalogenated to obtain unsaturated compounds. Example 1 of the said patent describes the dimerization of 1,2-dichloro-1,2,2-trifluoroiodoethane CClFI—$CClF_2$ in the presence of ultraviolet light and mercury to give CFC 316, which, in turn, is dechlorinated to perfluoro-1,3-butadiene with zinc dust. This process has the drawback of using mercury and an iodinated alkane, which are toxic compounds requiring the implementation of particular safety norms for their use in plants.

Patent application EP 1 247 791 describes the deiodofluorination of α,ω-diiodoperfluoroalkanes using zinc metal and nitrogenous organic compounds to prepare perfluoroalkanedienes. In particular, starting with 1,4-diiodoperfluorobutane, perfluorobutadiene is obtained. The drawback of this process is that diiodoperfluoroalkanes, which are toxic compounds, need to be used as starting materials. In addition, their synthesis is onerous from an industrial and safety viewpoint.

The abstract of patent RU 2 264 376 reports the pyrolysis of chlorotrifluoroethylene to give 1,2-dichlorohexafluorocyclobutane and 3,4-dichlorohexafluoro-1-butene. The latter compound is separated out by distillation and dechlorinated in the presence of zinc in a polar solvent to give perfluoro-1,3-butadiene. The drawback of this process is that the selectivity towards perfluoro-1,3-butadiene is low since the pyrolysis produces two main products that are difficult to separate.

The abstract of patent RU 2 272 017 describes the preparation of perfluoro-1,3-butadiene by dehalogenation of CFC 316 with zinc in aqueous medium at 30-90° C. The process is performed in the presence of acids such as $H_2SO_4$ or HCl or alternatively phase-transfer catalysts, for instance salts of weak acids. Tests performed by the Applicant have shown that this reaction has very slow kinetics.

There was thus seen to be a need for an industrial process for synthesizing perfluoro-1,3-butadiene, which has the following combination of properties:
- good selectivity in the individual steps,
- the precursors used are not CFCs, which, as is known, are banned by the Montreal Protocol,
- reduced formation of toxic by-products, for example to an amount of less than 2%.

One subject of the present invention is a process for preparing perfluoro-1,3-butadiene having the formula (I):

$$CF_2=CF-CF=CF_2 \quad (I)$$

comprising the following steps:
A) preparation of fluoro-halo-butanes of formula:

$$CF_2Y^I-CFY^{II}-CFY^{II}-CF_2Y^I \quad (V)$$

in which $Y^I$ and $Y^{II}$, which may be identical or different, may be H, Cl or Br, with the condition that $Y^I$ and $Y^{II}$ are not simultaneously hydrogen;
starting with a chloroolefin having the formula:

$$CY''Y=CY'Cl \quad (II)$$

in which Y, Y', Y", which may be identical or different, are H, Cl or Br, with the condition that Y, Y', Y" are not simultaneously hydrogen;
and performing the following two steps:
- a fluorodimerization, and
- a fluorination with elemental fluorine,
the order of the two steps also possibly being inverted,
- a dehalogenation or dehydrohalogenation step being performed between the two steps,
B) dehalogenation or dehydrohalogenation of the fluoro-halo compounds of formula (V) to give the compound perfluoro-1,3-butadiene of formula (I).

The olefins of formula (II) that may be used are preferably the following: $CHCl=CCl_2$, $CHCl=CHCl$, $CH_2=CCl_2$, $CCl_2=CCl_2$.

In step A), the fluorodimerization reaction is performed in liquid phase at temperatures of between −130° C. and 0° C. and preferably between −80° C. and −10° C.

This reaction produces one or more halofluorinated butanes having the following formulae:

$$CYY'F-CY'Cl-CY'Cl-CYY''F \quad (VII)$$

$$CY'ClF-CYY''-CYY''-CY'ClF \quad (VII')$$

$$CYY''F-CY'Cl-CYY''-CY'ClF \quad (VII'')$$

in which Y, Y', Y" have the meanings given above.

When the olefin of formula (II) is symmetrical, a single halo-fluorinated butane is formed and formulae (VII), (VII') and (VII") coincide.

The compounds of formula (VII), (VII') and (VII") that may be obtained are, for example, the following:

$CFHCl-CCl_2-CCl_2-CFHCl$, $CFCl_2-CHCl-CHCl-CFCl_2$, $CFHCl-CCl_2-CHCl-CFCl_2$, $CFHCl-CHCl-CHCl-CFHCl$, $CFCl_2-CCl_2-CCl_2-CFCl_2$, $CH_2F-CCl_2-CH_2F$, $CFCl_2-CH_2-CH_2-CFCl_2$, $CH_2F-CCl_2-CH_2-CFCl_2$.

This reaction may be performed by feeding elemental fluorine diluted with an inert gas (helium, nitrogen, etc.) into the reactor containing a liquid phase preferably composed of the pure olefin, optionally dissolved in the minimum required amount of an inert solvent when the olefin is in solid form at the reaction temperature. Preferably, the inert gas/$F_2$ volume dilution is between 80/1 and 6/1 and preferably between 50/1 and 10/1.

To obtain good selectivity, the olefin (II) during the fluorodimerization reaction is generally in excess relative to the number of moles of fluorine fed in. The olefin is preferably used pure or as a concentrated solution in the organic solvents indicated below. The fluorine is fed in in diluted form.

Organic solvents that are inert and in liquid form under the reaction conditions may optionally be used in the fluorodimerization. The organic solvents are chosen from the following: (per)fluoropolyethers, for example Galden®, (per)fluoroalkanes, for example containing from 3 to 10 carbon atoms, provided that they are liquid under the reaction conditions; hydrofluorocarbons (HFCs), hydrochlorofluorocarbons (HCFCs), perfluoroamines, hydrofluoroethers or hydrofluoropolyethers, for example mention may be made of H-Galden®, hydrochlorofluoroethers, chlorofluoroethers, or mixtures thereof.

In step A), the fluorination reaction with elemental fluorine of the chloroolefin of formula (II) is performed via addition of fluorine gas, optionally in the presence of an inert diluent such as $N_2$, He, etc. Generally, the fluorine/inert diluent ratio ranges from 1:0 to 1:5. The chloroolefin is diluted using organic solvents, or mixtures thereof, which are inert and in liquid form under the conditions of this step. The solvents that may be used are those mentioned in the fluorodimerization step.

Generally, the fluorination of the chloroolefin is performed at temperatures of between −120° C. and +50° C. and preferably between −90° C. and +30° C.

In step A), the dehydrohalogenation (removal of HCl or HBr) takes place, for example, via reaction with an inorganic base, preferably NaOH or KOH, or an organic base, preferably primary, secondary or tertiary alkyl or aryl amines. Generally, this step is performed in liquid phase in the presence of a solvent, preferably water or an alcohol, for example containing from 1 to 3 carbon atoms. When aqueous inorganic bases are used, the reaction may be performed in the presence of a quaternary ammonium or phosphonium salt, for instance tetrabutyl ammonium or phosphonium, preferably the chloride, trioctylbenzyl ammonium or phosphonium, preferably the chloride, etc. Alternatively, or as a mixture with the quaternary ammonium or phosphonium salts, other salts may be used, for instance sulfonium salts.

In step A), the dehalogenation (removal of chlorine or bromine) is performed by reaction with transition metals such as zinc, copper, manganese or metal couples such as Zn/Cu, Zn/Sn or Zn/Hg, in the presence of hydrogenated protic solvents, for instance aliphatic alcohols; or alternatively hydrogenated ether solvents, for instance glyme or dioxane; dipolar aprotic solvents, for instance DMF or DMSO. The solvents that are used must be liquid at the reaction temperature.

The dehalogenation and dehydrohalogenation are performed at temperatures of between 0 and 150° C. and preferably between 25° C. and 100° C.

In step B), the dehalogenation or dehydrohalogenation of the compounds of formula (V) is performed as described in step A).

In the process of the present invention, the pressure is not critical, and the process is preferably performed at atmospheric pressure.

The process of the invention may be performed in batch, semi-continuous or continuous mode for one or more of the individual reactions.

For example, the fluorodimerization may be performed as a continuous process in which fluorine gas, preferably diluted with an inert gas, and the olefin (II) are fed into the reactor, until the steady state is reached. In practice, the reagents are fed into the reactor at known rates and the reaction mixture is withdrawn continuously. The steady state is reached when the concentrations of the reagents and of the reaction products in the reactor are equal to the concentrations of the reagents and products leaving the reactor. For example, the mole ratio of $F_2$/olefin feed may range from 0 to 0.01.

The fluorination step may be performed via a semi-continuous process.

In greater detail, one embodiment of the present invention for the preparation of perfluoro-1,3-butadiene of formula (I) in which, in step A), fluorodimerization is used as the first step, is as follows:

step A):
1) formation of one or more halofluorobutanes by fluorodimerization of the chloroolefin of formula (II),
2) dehalogenation or dehydrohalogenation of the compound(s) obtained in step 1) to give halo-fluoro-butadienes of formula:

$$CFY^I=CY^{II}—CY^{II}=CFY^I \quad (IV)$$

in which $Y^I$, $Y^{II}$ have the meanings given above;
3) fluorination with elemental fluorine of the halo-fluoro-butadienes of formula (IV) into fluoro-halo-butanes of formula:

$$CF_2Y^I—CFY^{II}—CFY^{II}—CF_2Y^I \quad (V)$$

in which $Y^I$ and $Y^{II}$ are as defined above;
step B):
4) dehalogenation or dehydrohalogenation of the fluoro-halo compounds of formula (V) to give the compound perfluoro-1,3-butadiene of formula (I).

In step 1), one or more halofluorinated butanes of formulae (VII), (VII') and (VII") are obtained.

In step 2), dehydrohalogenation of the halofluorinated butanes, for example having the formulae (VII), (VII') and (VII"), takes place.

The dehalogenation of the halofluorinated butanes, for example having the formulae (VII), (VII') and (VII") takes place in step 2 as an alternative to the dehydrohalogenation.

Examples of compounds of formula (IV) that may be obtained in step 2) are the following: CFCl=CCl— CCl=CFCl, CFCl=CH—CH=CFCl, CHF=CCl— CCl=CHF, CHF=CCl—CH=CFCl.

In the fluorination step 3), compounds of formula (V) are obtained, for example the following: $CF_2Cl—CFCl— CFCl—CF_2Cl$, $CF_2Cl—CHF—CHF—CF_2Cl$, $CHF_2— CFCl—CFCl—CHF_2$, $CHF_2—CFCl—CHF—CF_2Cl$.

The fluorination step 3) may be performed, for example, via a semi-continuous process. In this case, fluorine gas per se or as a low dilution with an inert gas, for example a 1:1 dilution, and the compound of formula (IV) are fed into the reactor containing the reaction solvent or the mixture of reaction solvents.

In step B), step 4) of dehydrohalogenation or dehalogenation of one or more fluorohalobutanes of formula (V) leads to the production of the compound of formula (I).

The Applicant has found, surprisingly and unexpectedly, that the process of the present invention according to this first embodiment makes it possible to obtain good selectivity in each individual step.

In a second embodiment of the process of the present invention, the perfluorobutadiene may be obtained via a synthesis comprising the following steps:
step A):
$1^I$) fluorination with elemental fluorine of a chloroolefin having the formula (II), to give a fluorohaloethane of formula:

$$CFY''Y—CFY'Cl \quad (III)$$

in which $Y'$, $Y''$ are as defined above,
$2^I$) dehalogenation or dehydrohalogenation of the fluorohaloethane of formula (III), to give halo-fluoro-ethylenes of formula:

$$CFY^I=CFY^{II} \quad (VI)$$

in which $Y^I$, $Y^{II}$ are as defined above,
$3^I$) fluorodimerization of the halo-fluoro-ethylenes of formula (VI), to give fluorohalobutanes of formula:

$$CF_2Y^I—CFY^{II}—CFY^{II}—CF_2Y^I \quad (V)$$

when $Y^I=Y^{II}=Cl$ or Br,
and giving compound (V) as a mixture with $$CF_2Y^I—CFY^{II}—CFY^I—CF_2Y^{II} \quad (V')$$

$$CF_2Y^{II}—CFY^I—CFY^I—CF_2Y^{II} \quad (V'')$$

when $Y^I$ is other than $Y^{II}$,
step B):
$4^I$) dehalogenation or dehydrohalogenation of the fluoro-halo-butanes of step $3^I$).

The compounds of formula (III) that may be obtained in step $1^I$) are, for example, the following: $CHFCl—CFCl_2$ (HCFC 122a), $CHFCl—CHFCl$ (HCFC 132), $CFCl_2— CFCl_2$ (CFC 112), $CFCl_2—CH_2F$ (HCFC 132c).

The Applicant has found, surprisingly and unexpectedly, that during step $1^I$), only the products of 1,2 addition of fluorine to the olefinic double bond are obtained. For example, in the case of the addition of fluorine to tetrachloroethylene, CFC 112 is formed selectively, and CFC 112a in amounts of less than 2% by weight.

In step $2^I$), the dehydrohalogenation or dehalogenation is performed as described above.

The olefins of formula (VI) that may be obtained in this step are, for example, the following: CFCl=CFCl (CFC 1112), CFCl=CHF (HCFC 1122).

The Applicant has found, surprisingly and unexpectedly, that the dechlorination of CFC 112 obtained in step $1^I$) described above, in the case where the olefin (II) is tetrachloroethylene, leads to the formation of CFC 1112 with reduced amounts of CFC 1112a. In point of fact, as is well known, the latter is a toxic compound.

As stated in step $3^I$), to achieve good selectivity, during the reaction the olefin must always be in excess relative to the number of moles of fluorine fed in, and the inert gas/fluorine molar dilution is between 80/1 and 6/1 and preferably between 50/1 and 10/1.

Examples of compounds of formulae (V), (V') and (V") that may be obtained in step $3^I$) are:

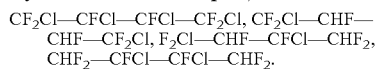

In step $4^I$), dehydrohalogenation or dehalogenation of one or more fluorohalobutanes of formula (V), (V') or (V") takes place.

The process that constitutes the second embodiment of the present invention may be performed in batch, semi-continuous or continuous mode for one or more of the individual steps $1^I$)-$4^I$).

Step $1^I$) may, for example, be performed in semi-continuous mode. In this case, fluorine gas, per se or as a low dilution of an inert gas, for example $F_2$/inert gas 1:1-1:3, and the compound of formula (II) are fed into the reactor, containing the reaction solvent or the mixture of reaction solvents, chosen from the solvents indicated above for the fluorination step.

Step $3^I$) may be performed as a continuous process in which fluorine gas, optionally diluted with an inert gas, and the olefin (VI) are fed into the reactor, until the steady state is reached. See in particular the description given above of the fluorodimerization performed continuously. The mole ratio of fluorine/olefin feed ranges from 1 to 0.01.

As stated, the process of the present invention is industrially very advantageous since the starting materials used do not belong to the class of chlorofluorocarbons (CFCs), and is characterized by good selectivity in each individual step of the synthesis.

In addition, the compounds that may be obtained in the individual steps may be obtained without using onerous processes for separating out by-products.

Another advantage of the process of the present invention lies in the fact that it is possible to recycle the unreacted starting material when the conversion of the starting material is incomplete, for example less than 50%.

The examples that follow illustrate the invention in a non-limiting manner.

EXAMPLES

Example 1

Step 1): Batch Fluorodimerization of Trichloroethylene (TCE) and Production of Fluorohalobutanes $C_4H_2F_2Cl_6$ 50.5 g of $CHCl=CCl_2$ (TCE) were placed in a 50 ml AISI 316 reactor. While maintaining the temperature at −50° C., 1 Nl/h of fluorine diluted with 10 Nl/h of helium was added until a final TCE/$F_2$ mole ratio=6.6 was obtained. The crude reaction product was analysed by GC and by $^{19}F$—NMR. The TCE conversion was 24% and the $C_4H_2F_2Cl_6$ dimer selectivity was 60%.

The unconverted TCE is recovered by distillation. 36 g of the compound are recovered, and may be reused.

Example 2

Step 1): Continuous Fluorodimerization of Trichloroethylene (TCE) to $C_4H_2F_2Cl_6$.

73.6 g of TCE were placed in a 45 ml AISI 316 reactor equipped with a discharge vent. While maintaining the temperature at −50° C., TCE was added at a rate of 18.0 g/h and 0.45 Nl/h of fluorine diluted with 4.5 Nl/h of helium were added so as to have a TCE/$F_2$ mole ratio=6.8. The test was performed continuously for 11 hours 45 minutes, collecting the mixture of products and reagents leaving the reactor. The crude reaction product in the working reactor (66.2 g) was discharged and analysed by GC, GC-MS and $^{19}F$—NMR. The TCE conversion is 22.9% and the selectivity towards $C_4H_2F_2Cl_6$ is 50%.

Example 3

Step 2): Dehydrochlorination of the $C_4H_2F_2Cl_6$ Dimers to $CFCl=CCl—CCl=CFCl$ 139 g of $C_4H_2F_2Cl_6$ were placed in a round-bottomed flask equipped with a magnetic stirrer, two dropping funnels, a thermometer and a condenser. 8.6 g of Aliquat 336 were added at room temperature, followed by dropwise addition of 175 ml of 20% NaOH with vigorous stirring, the dropping rate being adjusted so that the temperature does not exceed 35° C. The conversion was monitored by GC. After 8 hours, the reaction was complete (total conversion) and the organic phase was separated out and analysed by GC, GC-MS and $^{19}F$—NMR. The reaction yield for $CFCl=CCl—CCl=CFCl$ is 93%.

Example 4

Step 3): Fluorination of $CFCl=CCl—CCl=CFCl$ to $CF_2Cl—CFCl—CFCl—CF_2Cl$ (CFC 316)

50.1 g of $CF_3OCFClCF_2Cl$ as solvent were placed in a 50 ml AISI 316 reactor maintained at a temperature of 10° C., and 2.7 Nl/h of fluorine diluted with 0.75 Nl/h of helium and 9.4 g/h of $CFCl=CCl—CCl=CFCl$ were fed in over 1 hour. The crude reaction product was discharged and analysed by GC, GC-MS and $^{19}F$—NMR. The conversion of the $CFCl=CCl—CCl=CFCl$ is 97.8% and the selectivity towards CFC 316 is 64%.

Example 5

Step 4): Dechlorination of CFC 316 to Perfluoro-1,3-Butadiene.

120 g of 2-propanol and 40 g of zinc were placed in a 250 ml three-necked round-bottomed flask equipped with a magnetic stirrer, a thermometer, a dropping funnel and a Vigreux column connected to a trap at −80° C. The mixture was heated to 80° C., and 80 g of CFC 316 were then added dropwise to the flask with stirring. The perfluoro-1,3-butadiene began to distil after a few minutes. The dropwise addition of CFC 316 was complete after 1 hour, and stirring was continued until the distillation of the perfluoro-1,3-butadiene was complete. The product collected in the trap was identified and characterized, by GC and $^{19}F$—NMR, as perfluoro-1,3-butadiene (96.4% pure). The reaction yield is 95%. The product is distilled on a 60-plate column. The distillation yield is 96%. The product obtained is 99.5% pure.

Example 6

Step $1^I$): Addition of Elemental Fluorine to Trichloroethylene and Formation of $CHClF—CCl_2F$ (CFC 122a)

A solution consisting of 25.5 g of trichloroethylene (TCE) and 475 g of $CF_3O—CFCl—CF_2Cl$ as reaction solvent is placed in a 400 ml AISI 316 reactor equipped with a mechanical stirrer.

The solution is cooled, using a cryostat, to a temperature of −70° C. and one mole of elemental fluorine diluted with nitrogen in a 1/2 mole ratio is fed in via a drip feed. 1.07 mol of TCE are simultaneously fed in via a pump. The reagents are fed in over 8 hours, while maintaining the temperature at −70° C.

At the end of the reaction, 633 g of a solution are discharged and analysed by GC/MS (gas chromatography coupled to mass spectrometry). The conversion of the TCE is equal to 75% and the selectivity towards CFC 122a (CHClF—CCl$_2$F) is 56.7%.

Example 7

Step 2$^I$): Dehydrochlorination of CFC 122a Obtained in Example 6 to Give CClF=CClF (CFC 1112)

90 g of CFC 122a obtained in Example 6, with a purity of 94%, and 5 g of tetrabutylammonium hydroxide are placed in a 250 ml 4-necked reactor equipped with a magnetic stirrer, a dropping funnel, a thermometer and a water-cooled condenser. 26 g of aqueous 20% NaOH solution are added with stirring, while restricting the exothermicity to 30° C. with an ice-water bath. Once the addition of the sodium hydroxide is complete, the mixture is left stirring at 30° C. for a further 40 minutes. The resulting mixture is cooled to 10° C.: the final mixture has two separate phases. The reaction mixture is poured into a separating funnel maintained at a temperature of 10° C. 72 g of the higher-density organic phase are separated out, consisting of the 99% pure compound (65 g) CFC 1112 (FCCl=CClF). 100% conversion, 98% yield.

Example 8

Step 3$^I$): Fluorodimerization of CFC 1112 to Give CClF$_2$—CClF—CClF—CClF$_2$ (CFC 316)

50 g of 1,2-dichloro-1,2-difluoroethylene are placed in a 50 ml reactor. 1 Nl/h of fluorine and 15 Nl/h of nitrogen are fed in continuously at a temperature of −70° C. After 135 minutes, the feeding is stopped so that the final olefin/F$_2$ ratio is 3.7. The crude reaction product is analysed quantitatively by GC and $^{19}$F—NMR analysis. The conversion is 43% and the selectivity towards CFC 316 is 70%.

Example 9

Step 4$^I$): Dechlorination of CFC 316 to Perfluoro-1,3-Butadiene.

120 g of 2-propanol and 40 g of zinc were placed in a 250 ml three-necked round-bottomed flask equipped with a magnetic stirrer, a thermometer, a dropping funnel and a Vigreux column connected to a trap at −80° C. The mixture was heated to 80° C., and 80 g of CFC 316 were then added dropwise to the flask with stirring. The perfluoro-1,3-butadiene began to distil after a few minutes. The dropwise addition of CFC 316 was complete after 1 hour, and stirring was continued until the distillation of the perfluoro-1,3-butadiene was complete. The product collected in the trap was identified and characterized, by GC and $^{19}$F—NMR, as perfluoro-1,3-butadiene (96.4% pure). The reaction yield is 95%. The product is distilled on a 60-plate column. The distillation yield is 96%. The product obtained is 99.5% pure.

Example 10

Step 1$^I$): Addition of Elemental Fluorine to Tetrachloroethylene (PCE)

50.9 g of CF$_3$O—CFCl—CF$_2$Cl as reaction solvent are placed in the same reactor used in Example 8. The reactor is cooled, using a cryostat, to a temperature of −30° C., and a solution of PCE at 50% by weight in CF$_3$O—CFCl—CF$_2$Cl solvent is fed in, via a drip feed, at a rate of 5.04 g/h. 2.22 Nl/h of fluorine gas are simultaneously fed in, via another drip feed. The fluorine is fed in diluted with nitrogen in a 1/2 fluorine/nitrogen mole ratio.

The reaction is conducted for 3 hours and the final solution is analysed by GC/MS. The PCE conversion is quantitative. Selectivity, expressed in mol %, towards CCl$_2$F—CCl$_2$F (CFC 112) is 81%. CFC 112a is present in the reaction mixture in small amount (0.5% relative to the CFC 112).

Example 11

Step 2$^I$): Dechlorination of CFC 112 Obtained in Example 10

60.0 g of zinc dust, activated by washing with 3 N HCl solution, and 500 ml of isopropanol are placed, under an inert atmosphere of nitrogen, in a 1-litre 3-necked reactor equipped with a magnetic stirrer, a dropping funnel and a thermometer, and connected via a Vigreux column and a water-cooled condenser to a cold trap maintained at a temperature of −75° C. The internal temperature is brought to 75° C. 114 g of FCCl$_2$CCl$_2$F, obtained as described in Example 5 and subsequently purified by fractional distillation to a purity of 99%, are then added dropwise. Once the addition is complete, the mixture is left stirring for 1 hour at 80° C. 67.9 g of CFC 1112 are collected in the cold trap. The yield of CFC 1112 is equal to 92%.

The invention claimed is:

1. A process for preparing perfluoro-1,3-butadiene, comprising the following steps:
    A) the preparation of fluoro-halo-butanes of formula:

$$CF_2Y^I\text{—}CFY^{II}\text{—}CFY^{II}\text{—}CF_2Y^I \quad (V)$$

in which each Y$^I$ and each Y$^{II}$, which are identical or different, are H, Cl or Br, with the condition that vicinal instances of Y$^I$ and of Y$^{II}$ are not simultaneously hydrogen;
    starting with a chloroolefin having the formula:

$$CY''Y=CY'Cl \quad (II)$$

in which Y, Y', Y", which are identical or different, are H, Cl or Br, with the condition that Y, Y', Y" are not simultaneously hydrogen;
    and performing the following two steps:
    a fluorodimerization, and
    a fluorination with elemental fluorine,
    wherein the fluorodimerization step is performed prior to the fluorination step,
    a dehalogenation or dehydrohalogenation step being performed between the two steps, and
    B) dehalogenation or dehydrohalogenation of the fluoro-halo compounds of formula (V) to give the compound perfluoro-1,3-butadiene.

2. The process according to claim 1, wherein, in the fluorodimerization, one or more halofluorinated butanes are obtained, having the following formulae:

$$CYY''F\text{—}CY'Cl\text{—}CY'Cl\text{—}CYY''F \quad (VII)$$

$$CY'ClF\text{—}CYY''\text{—}CYY''\text{—}CY'ClF \quad (VII'), or$$

$$CYY''F\text{—}CY'Cl\text{—}CYY''\text{—}CY'ClF \quad (VII'')$$

in which Y, Y', Y" have the meanings given in claim 1.

3. The process according to claim 2, wherein the halofluorinated butanes that are obtained are selected from the group consisting of:

CFHCl—CCl$_2$—CCl$_2$—CFHCl, CFCl$_2$—CHCl—CHCl—CFCl$_2$,

CFHCl—CCl$_2$—CHCl—CFCl$_2$, CFHCl—CHCl—CHCl—CFHCl,

CFCl$_2$—CCl$_2$—CCl$_2$—CFCl$_2$, CH$_2$F—CCl$_2$—CCl$_2$—CH$_2$F, and

CFCl$_2$—CH$_2$—CFCl$_2$—, CH$_2$F—CCl$_2$—CH$_2$—CFCl$_2$.

4. The process according to claim 1, wherein the fluorodimerization is performed by feeding elemental fluorine diluted with an inert gas into a reactor containing a liquid phase.

5. The process according to claim 4, wherein the inert gas/fluorine volume dilution is between 80/1 and 6/1.

6. The process according to claim 1, wherein in the fluorodimerization reaction, the olefin (II) is in excess relative to the number of moles of fluorine fed.

7. The process according to claim 4, wherein the liquid phase comprises the pure olefin or a concentrated solution of the olefin in organic solvents that are inert and in liquid form under the reaction conditions.

8. The process according to claim 7, wherein the organic solvents are selected from the group consisting of: (per)fluoropolyethers, (per)fluoroalkanes; hydrofluorocarbons (HFC), hydrochlorofluorocarbons (HCFC), perfluoroamines, hydrofluoroethers, and hydrofluoropolyethers.

9. The process according to claim 1, wherein, in step A), the dehydrohalogenation is performed by reacting the product of the fluorodimerization with an inorganic base or with an organic base, in liquid phase.

10. The process according to claim 9, wherein the dehydrohalogenation is performed in liquid phase in the presence of a solvent.

11. The process according to claim 9, wherein, when aqueous inorganic bases are used, the reaction is performed in the presence of a quaternary ammonium or phosphonium salt.

12. The process according to claim 1, wherein, in step A), the dehalogenation is performed via reaction with transition metals selected from the group consisting of zinc, copper, manganese, and metal couples, in the presence of solvents selected from the group consisting of hydrogenated protic solvents, hydrogenated ether solvents, and dipolar aprotic solvents, which are liquid at the reaction temperature.

13. The process according to claim 1, wherein, in step B), the dehalogenation or dehydrohalogenation of the compounds of formula (V) is performed via reaction with transition metals selected from the group consisting of zinc, copper, manganese, and metal couples, in the presence of solvents selected from the group consisting of hydrogenated protic solvents, hydrogenated ether solvents, and dipolar aprotic solvents, which are liquid at the reaction temperature.

14. The process according to claim 1, which is performed in batch, semi-continuous or continuous mode for one or more of the individual reactions.

15. The process according to claim 1, comprising the following steps:

step A):
1) formation of one or more halofluorobutanes by fluorodimerization of the chloroolefin of formula (II),
2) dehalogenation or dehydrohalogenation of the compound(s) obtained in step 1) to give halo-fluoro-butadienes of formula:

$$CFY^I=CY^{II}—CY^{II}=CFY^I \qquad (IV)$$

in which $Y^I$, $Y^{II}$ have the meanings given in claim 1;

3) fluorination with elemental fluorine of the halo-fluorobutadienes of formula (IV) into fluoro-halo-butanes of formula:

$$CF_2Y^I—CFY^{II}—CFY^{II}—CF_2Y^I \qquad (V)$$

in which $Y^I$ and $Y^{II}$ are as defined in claim 1;

step B):
4) dehalogenation or dehydrohalogenation of the fluorohalo compounds of formula (V) to give the compound perfluoro-1,3-butadiene of formula (I).

16. The process according to claim 15, wherein the compounds of formula (IV) that are obtained in step 2) are the following:

CFCl=CCl—CCl=CFCl, CFCl=CH—CH=CFCl,

CHF=CCl—CCl=CHF, or CHF=CCl—CH=CFCl.

17. The process according to claim 15, wherein the compounds of formula (V) that are obtained in step 3) are the following:

CF$_2$Cl—CFCl—CFCl—CF$_2$Cl, CF$_2$Cl—CHF—CHF—CF$_2$Cl, CHF$_2$—CFCl—CFCl—CHF$_2$, or CHF$_2$—CFCl—CHF—CF$_2$Cl.

* * * * *